United States Patent
Rolls et al.

(10) Patent No.: US 11,724,119 B2
(45) Date of Patent: Aug. 15, 2023

(54) METHODS OF NEURAL INHIBITION FOR TREATING BOWEL DISEASES AND DISORDERS

(71) Applicant: TECHNION RESEARCH & DEVELOPMENT FOUNDATION LIMITED, Haifa (IL)

(72) Inventors: Asya Rolls, Haifa (IL); Tamar Koren, Haifa (IL); Hilla Azulay-Debby, Haifa (IL); Tamar Ben Shaanan, Karmiel (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 252 days.

(21) Appl. No.: 16/768,974

(22) PCT Filed: Dec. 6, 2018

(86) PCT No.: PCT/IL2018/051339
§ 371 (c)(1),
(2) Date: Jun. 2, 2020

(87) PCT Pub. No.: WO2019/111261
PCT Pub. Date: Jun. 13, 2019

(65) Prior Publication Data
US 2021/0046324 A1 Feb. 18, 2021

Related U.S. Application Data

(60) Provisional application No. 62/595,189, filed on Dec. 6, 2017.

(51) Int. Cl.
*A61N 2/00* (2006.01)
*A61N 7/00* (2006.01)
(Continued)

(52) U.S. Cl.
CPC .......... *A61N 2/006* (2013.01); *A61N 1/36014* (2013.01); *A61N 5/0622* (2013.01); *A61N 7/00* (2013.01); *A61N 2007/0026* (2013.01)

(58) Field of Classification Search
CPC .......... A61N 2/004; A61N 2/006; A61N 2/02; A61N 2005/0609; A61N 2007/0026; A61N 5/0622; A61N 7/00
See application file for complete search history.

(56) References Cited

U.S. PATENT DOCUMENTS

2011/0082326 A1 4/2011 Mishelevich et al.
2013/0131753 A1 5/2013 Simon et al.
(Continued)

OTHER PUBLICATIONS

Exton et al., "Pavlovian conditioning of immune function: animal investigation and the challenge of human application", 2000, Behavioural Brain Research, 110, p. 129-141 (Year: 2000).*
(Continued)

*Primary Examiner* — Christine H Matthews
(74) *Attorney, Agent, or Firm* — The Roy Gross Law Firm, LLC; Roy Gross

(57) ABSTRACT

The present invention is directed to a method for treating a bowel disease in a subject in need thereof, the method comprising inhibiting the activity of neurons of the insular cortex of the subject. Further provided is a system comprising a transcranial stimulation transducing coil for transcranial stimulation configured to provide a series of pulses to neurons of the insular cortex.

18 Claims, 6 Drawing Sheets

(51) Int. Cl.
A61N 1/36 (2006.01)
A61N 5/06 (2006.01)

(56) References Cited

U.S. PATENT DOCUMENTS

| | | |
|---|---|---|
| 2013/0317580 A1 | 11/2013 | Simon et al. |
| 2014/0142669 A1 | 5/2014 | Cook et al. |
| 2014/0235927 A1 | 8/2014 | Zangen et al. |
| 2016/0001096 A1* | 1/2016 | Mishelevich ............ A61N 7/02 601/2 |
| 2016/0121114 A1 | 5/2016 | Simon et al. |
| 2017/0021161 A1 | 1/2017 | De Ridder |
| 2017/0246481 A1 | 8/2017 | Mishelevich |

OTHER PUBLICATIONS

Gorgolla, "The insular cortex", 2017, Current Biology, 27, R573-R591 (Year: 2017).*
PCT International Search Report for International Application No. PCT/IL2018/051339, dated Mar. 13, 2019, 18pp.
PCT Written Opinion for International Application No. PCT/IL2018/051339, completed Mar. 11, 2019, 5pp.
PCT International Preliminary Report on Patentability for International Application No. PCT/IL2018/051339, dated Jun. 9, 2020, 6pp.

* cited by examiner

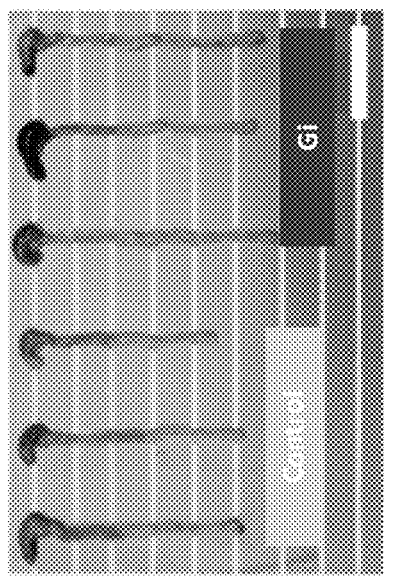
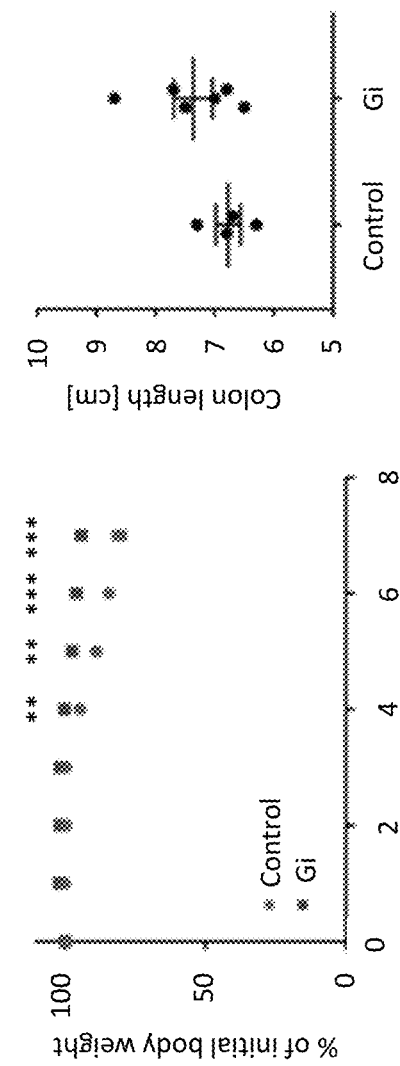
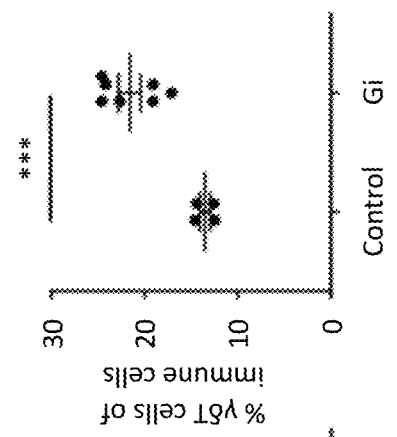
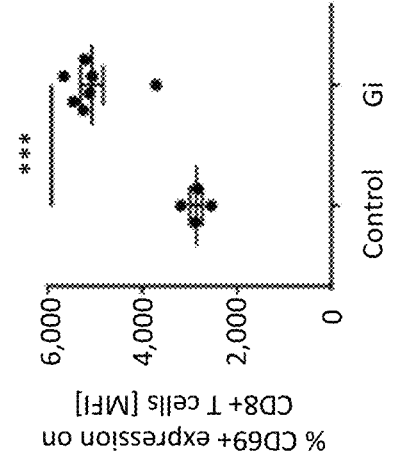
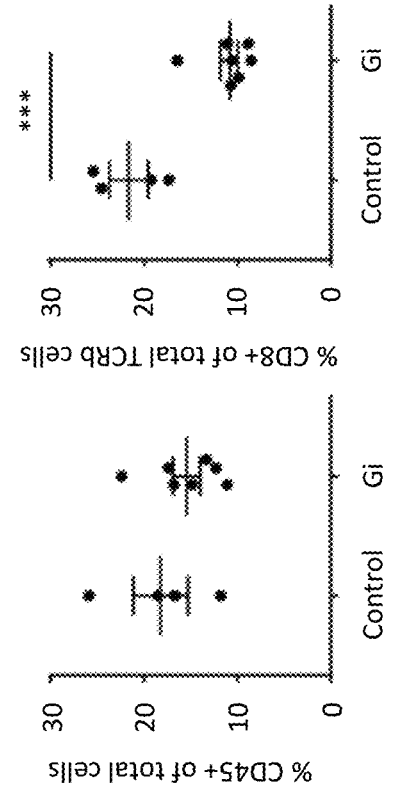
FIGURE 2B
FIGURE 2C
FIGURE 2D
FIGURE 2E
FIGURE 2F
FIGURE 2G

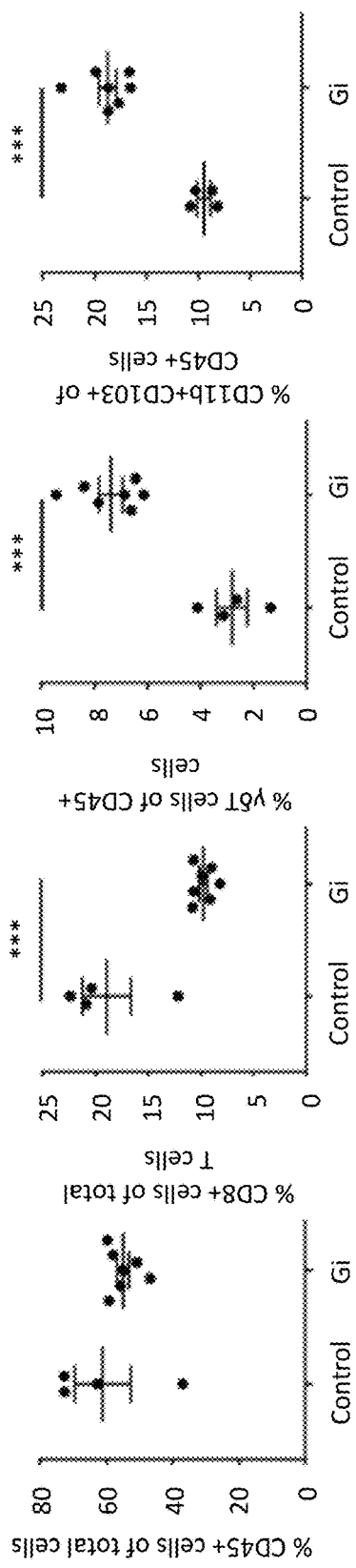
FIGURE 2H  FIGURE 2I  FIGURE 2J  FIGURE 2K
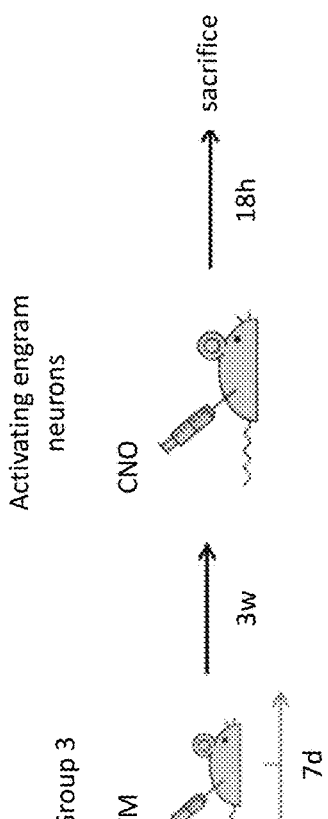
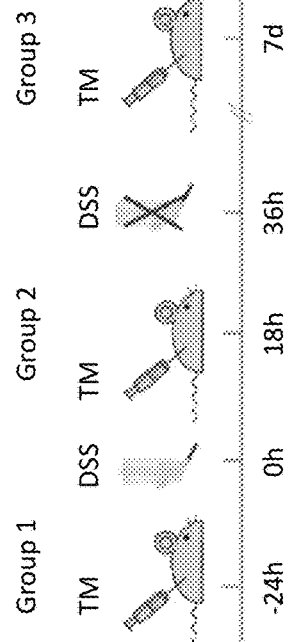
FIGURE 3A

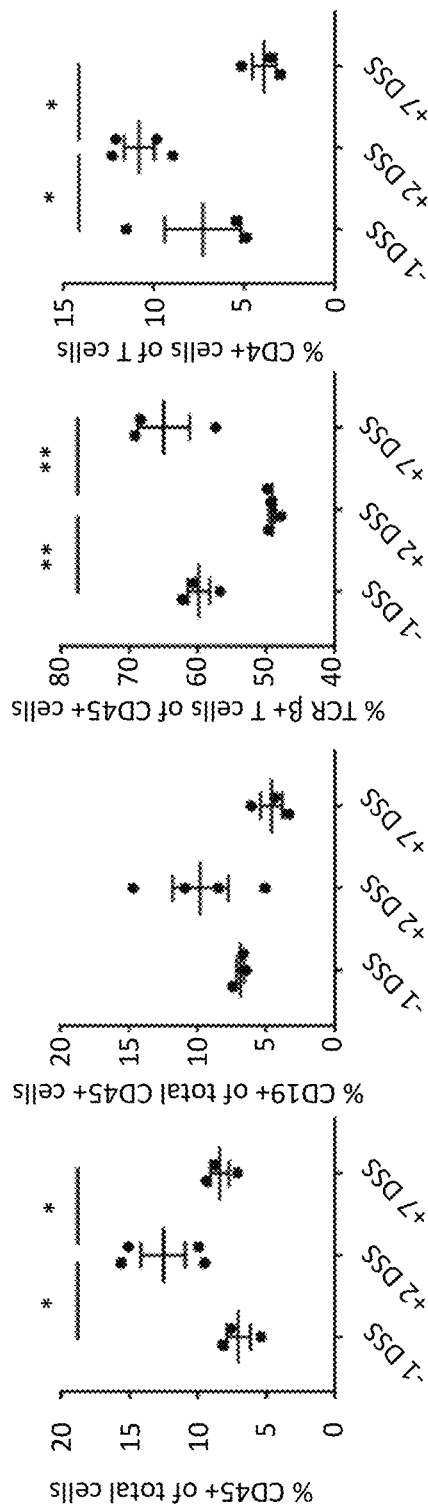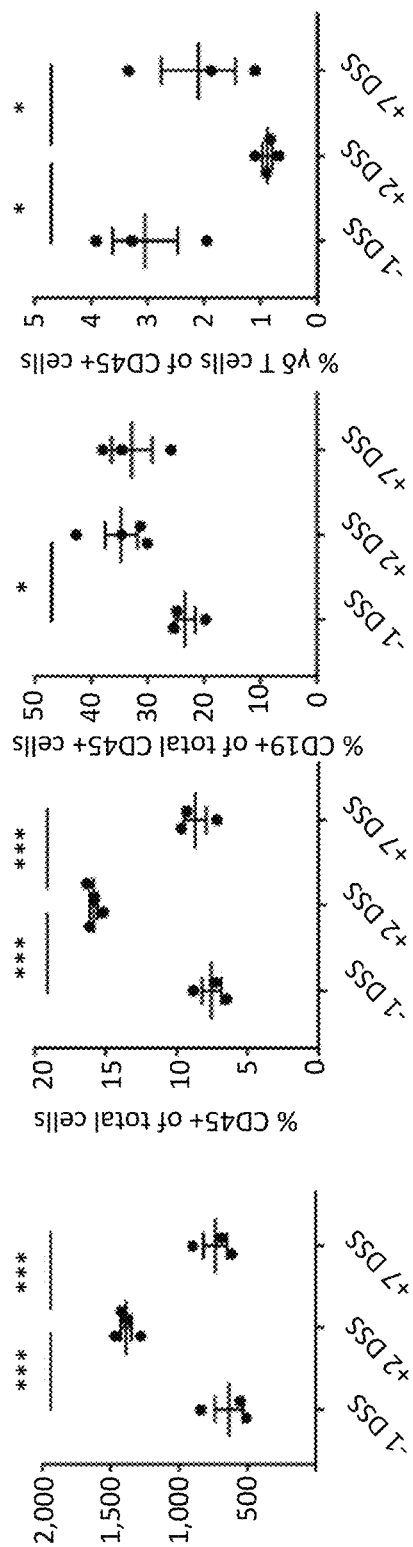

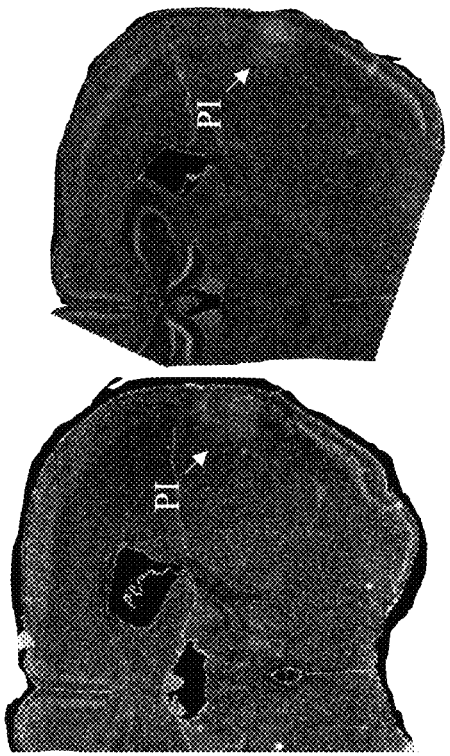
FIGURE 4A
FIGURE 4B
FIGURE 4C
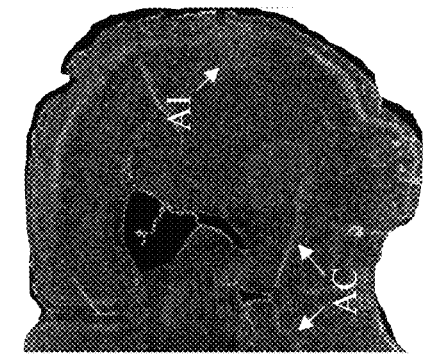
FIGURE 4D
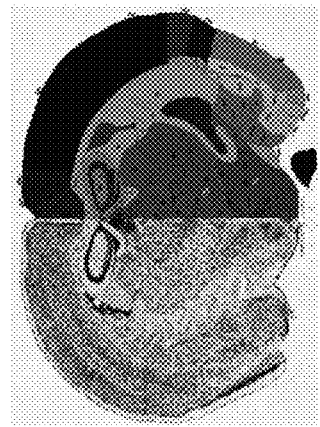
FIGURE 4E
FIGURE 4F
FIGURE 4G
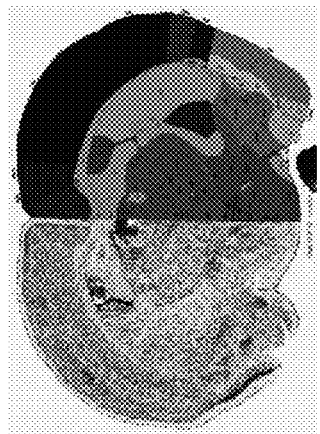
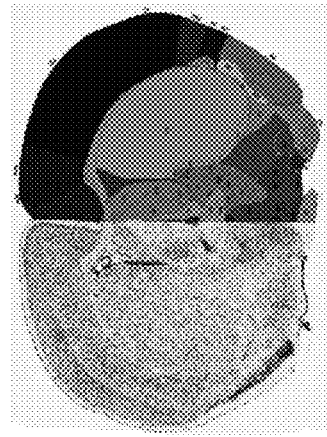
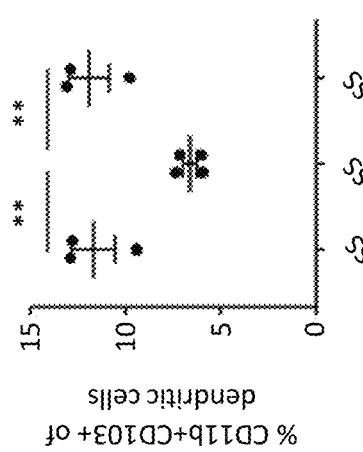
FIGURE 3J

METHODS OF NEURAL INHIBITION FOR TREATING BOWEL DISEASES AND DISORDERS

CROSS REFERENCE TO RELATED APPLICATIONS

This application is a National Phase of PCT Patent Application No. PCT/IL2018/051339 having International filing date of Dec. 6, 2018, which claims the benefit of priority of U.S. Provisional Patent Application No. 62/595,189 filed Dec. 6, 2017, the contents of which are incorporated herein by reference in their entirety.

FIELD OF INVENTION

The present invention is related to methods of treatment of bowel diseases.

BACKGROUND OF THE INVENTION

The insular cortex is known as an interoceptive site taking part in integration of the sense of the physiological condition of the body. It receives and integrates a wide range of inputs from the periphery, such as thirst, hunger and visceral sensations, as well as signals deriving from the gastrointestinal tract.

Inflammatory bowel diseases (IBD), which include Crohn's disease and ulcerative colitis (UC), is a relapsing and remitting condition characterized by chronic inflammation at various sites in the gastrointestinal tract (GI), which results in diarrhea and abdominal pain. Bowel inflammation results from a cell-mediated immune response in the GI mucosa. The precise etiology is unknown, but evidence suggests that the normal intestinal flora trigger an abnormal immune reaction in patients with a multifactorial genetic predisposition. No specific environmental, dietary, or infectious causes have been identified.

Irritable bowel syndrome (IBS), is a disease characterized by recurrent abdominal discomfort or pain. IBS is clinically diagnosed in patients. Patients diagnosed with IBS must be afflicted by at least two phenotypes related to: defecation, altered frequency of stool, or altered consistency of stool. The cause is currently unknown.

SUMMARY OF THE INVENTION

The present invention, in some embodiments thereof, is directed to a method of treating or ameliorating a bowel disease in a subject in need thereof, comprising the step of inhibiting the activity of neurons in the insular cortex of the subject including, but not limited to, transcranial magnetic stimulation (TMS), biofeedback stimulation and focused ultrasound stimulation (FUS). The present invention further provides a method for reducing an immune response in a subject, comprising the step of inhibiting neurons in the insular cortex of the subject with, thereby reducing an immune response in a subject.

In another embodiment, the present invention further provides a method for treating an inflammatory disease or disorder in a subject in need thereof.

In another embodiment, the present invention further provides a method for reducing an immune response in a subject in need thereof, by inhibiting neurons in the insular cortex, so as to modulate the activity, the abundance or both of a CD8 T-cell, a CD4 T-cell, a γδ T-cell, a B-cell, a dendric cell or any combination thereof.

According to one aspect, there is provided a method for treating a bowel disease in a subject in need thereof, the method comprising inhibiting the activity of neurons of the insular cortex of the subject, thereby treating a bowel disease in the subject.

In some embodiments, the neurons of the insular cortex are in coordinates: (a) Medial Lateral (ML): (2.5)-(+4.5) cm; (b) Anterior Posterior (AP): (3.0)-(−2.2) cm; and (c) Dorsal Ventral (DV): (−1)-(+2) cm.

In some embodiments, the activity of the insular neurons in the cortex is inhibited by applying transcranial magnetic stimulation (TMS).

In some embodiments, the activity of the insular neurons in the cortex is inhibited by applying biofeedback stimulation.

In some embodiments, the activity of the insular neurons in the cortex is modified by applying focused ultrasound stimulation (FUS).

In some embodiments, the subject is afflicted with Crohn's disease. In some embodiments, the subject is afflicted with ulcerative colitis (UC). In some embodiments, the subject is afflicted with an immunodeficient disease. In some embodiments, the subject is afflicted with an autoimmune disease. In some embodiments, the subject is afflicted with a functional gastrointestinal disorder (FGID) or a symptom thereof. In some embodiments, FGID is irritable bowel syndrome (IBS).

In some embodiments, inhibiting neurons of the insular cortex results comprises altering activity, abundance or both of a CD8 T-cell, a CD4 T-cell, a γδ T-cell, a B-cell, a dendritic cell, or any combination thereof.

In some embodiments, inhibiting neurons of the insular cortex is reducing the number of: CD4 and CD45+ T cells and B cells in the intraepithelial layer of the subject.

In some embodiments, inhibiting neurons of the insular cortex is reducing the number of: CD4 and CD45+ T cells and B cells in the lamina propria of the subject.

In some embodiments, inhibiting the activity of neurons of the insular cortex is increasing the number of γδT cells in the lamina propria of the subject.

According to another aspect, there is provided a system comprising a transcranial stimulation transducing coil for transcranial stimulation configured to provide a series of pulses to neurons of the insular cortex of a subject, wherein the neurons of the insular cortex are in coordinates: (a) ML: (2.5)-(+4.5) cm; (b) AP: (3.0)-(−2.2) cm; and (c) DV: (−1)-(+2) cm.

In some embodiments, the system is for use in the treatment of a bowel disease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 2A-2K are illustrations, images and graphs showing that the inhibition of activity-dependent insular neurons alleviates local inflammation. (2A) is an illustration of a non-limiting scheme of an experimental design. (2B) is graphs showing body weight loss (percentages) of Gi vs. control group. Measurements were taken for 7 days throughout daily administration of dextran sodium sulfate (DSS) in drinking water and clozapine N-oxide (CNO; i.p). (2C) is a graph and an image showing colon length of Gi vs. control group. A shorter colon indicated increased severity of inflammation. (2D-2G) are graphs showing the differences in $CD45^+$ cells (2D), CD8+ T cells (2E), CD69 expressing CD8+ T cells (2F), and TCRγδ cells (2G) in intraepithelial layer (IEL), according to flow cytometry analysis. (2H-2K) are graph showing the differences in $CD45^+$ cells (2H), CD8+ T cells (2I), γδT cells (2J), and CD11b+CD103+ cells (2K) in lamina propria (LP), according to flow cytometry analysis. Data are represented as mean±s.e.m. from two independent experiments. *$P<0.0005$, **$P<0.0001$; according to unpaired two-tailed Student's t-test.

FIGS. 3A-3J are illustrations, images and graphs showing that the activation of activity-dependent insular neurons elicits a local inflammatory response. (3A) is an illustration of a non-limiting scheme of the experimental design. (3B-3F) are graphs showing the differences in $CD45^+$ cells (3B), CD19+ (3C), TCRβ+ T cells (3D), CD4+ (3E), and CD69 expressing CD4+ cells (3F) in IEL according to flow cytometry analysis. (3G-3J) are graphs showing differences in $CD45^+$ cells (3G), CD19+ (3H), and γδT cells (3I) in LP according to flow cytometry analysis. (3J) is a graph showing the changes in LP CD11b+CD103+ cells (i.e., dendritic cells), which were shown to have an opposite trend to the one presented in FIG. 2K. Data are represented as mean±s.e.m. from two independent experiments. *$P<0.05$, $P<0.005$, *$P<0.0005$, ****$P<0.0001$; according to unpaired two-tailed Student's t-test.

FIGS. 4A-4H are micrographs and images of sections of a mouse brain. (4A-4D) are representative micrographs of sections showing activity-dependent labeling of projections originating in the right posterior insula which were found to be responsive to the gut inflammation (mCherry, red). (4E-4H) are images taken from Allen's brain atlas corresponding to 4A-4D. (4A) projections are observed in the anterior insula (AI) and anterior commissure (AC). (4B-4C) Site of injection, as seen by the mCherry fluorescent labeling of neuronal cell bodies in the posterior insula (PI). (4D) Projections seen in the temporal association cortex (TAC), ectorhinal, perirhinal and entorhinal area and the amygdala (AM).

DETAILED DESCRIPTION OF THE INVENTION

Figure 1:
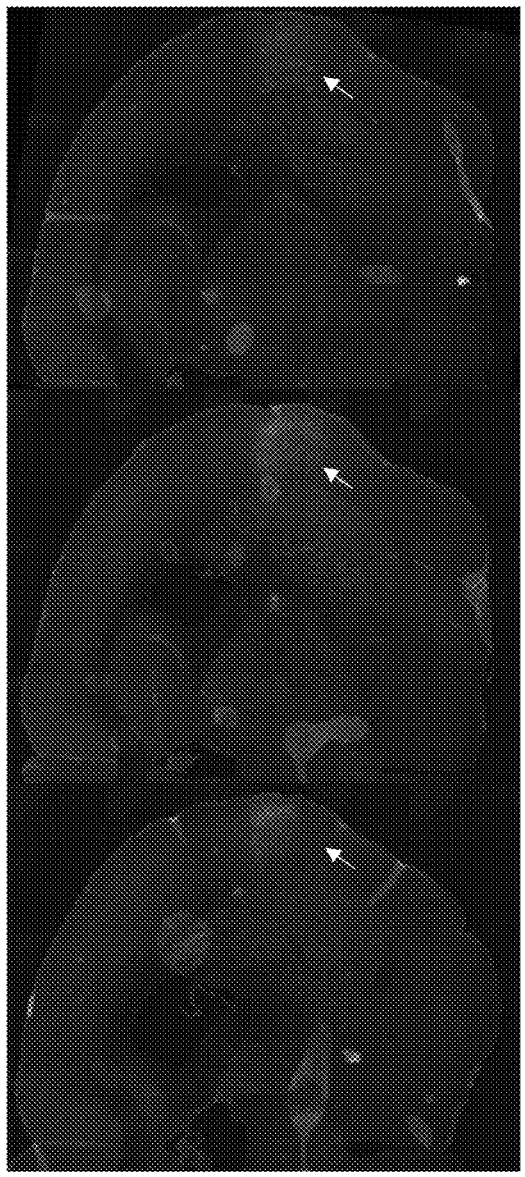
FIG. 1 is serial micrographs showing the activity dependent labeling (mCherry) of neurons in the right posterior dorsal insula of a mouse brain. Site of viral vector injection (anterior-posterior −0.36, medial-lateral 4.00, dorsal-ventral −3.85). Neurons that were active during colon inflammation in $Fos^{CreER}$ mice, expressed Cre-recombinase. Tamoxifen allowed the recombination to occur (for a time window of 24 hours) on the injected target gene, encoding for mCherry fluorescence protein (arrow).

The present invention is directed to treating or ameliorating bowel disease in a subject in need thereof, the method comprising inhibiting the activity neurons of the insular cortex of the subject, thereby treating or ameliorating the bowel disease in the subject.

The present invention further provides a method for reducing an immune response in a subject, comprising the step of inhibiting the activity of neurons in the insular cortex of the subject, thereby reducing an immune response in a subject.

In another embodiment, the present invention further provides a method for treating an inflammatory disease or disorder in a subject in need thereof.

The present invention is based, in part, on the finding that reducing specific neurons activity reverted gut pathophysiological manifestations (e.g., inflammatory response) in mice. Specifically, neurons of the insular cortex region were found to be a part of the brain's peripheral input receivers of immune-related information. As exemplified herein, reactivating a specific insular neuron engram which was recorded in the past under a gut inflammation episode, had induced recurrence of the inflammatory response. The invention is further based, in part, on the finding that by artificially reducing specific engrams of neurons of the insular cortex by reverting them to their pre-inflammatory state (e.g., reduced inflammatory state), promotes a therapeutic response relevant for inflammatory diseases and other immune-related diseases.

As used herein, "engram" refers to a permanent bio-chemical and-physical changes in the brain, or other neural tissue, which occur in response to external stimuli. In another embodiment, bio-chemical and-physical changes provide the means for the existence of a memory. In another embodiment, an engram is a memory trace. In another embodiment, learning activates a small ensemble of brain cells, inducing in these cells persistent physical/chemical changes. In another embodiment, reactivation of these cells by relevant recall cues results in retrieval of the specific memory.

The present invention provides, in one embodiment, a method for reducing an immune response in a subject, comprising the step of inhibiting the activity of neurons in the insular cortex region of the subject, thereby reducing an immune response in a subject. In another embodiment, modulating an immune response is decreasing, inhibiting, differentially inhibiting, or any combination thereof, an immune response.

As used herein, "insular neurons" are neurons of the insular cortex. In another embodiment, insular neurons are found in the right hemisphere of the brain. In another embodiment, insular neurons are found in the left hemisphere of the brain. In another embodiment, insular neurons are found in both hemispheres of the brain. In another embodiment, insular neurons are found in the cerebral cortex. In another embodiment, insular neurons are folded within the lateral sulcus. In another embodiment, the insula is responsible for regulation of homeostasis. In another embodiment, the insula is divided into anterior and posterior insula. In another embodiment, the insula is divided into a larger and a smaller insula. In another embodiment, the anterior insula is the larger insula. In another embodiment, the posterior insula is the smaller insula. In another embodiment, the insular is located medially to the opercula of insula.

In some embodiments, the method comprises inhibiting insular neurons located in the following coordinates medial lateral (ML): (2.5)-(+4.5) cm; anterior posterior (AP): (3.0)-(−2.2) cm; dorsal ventral (DV): (−1)-(+2) cm. In some embodiments, inhibiting insular neurons located in the hereinabove coordinates further projects to other areas of the brain. In some embodiments, inhibiting insular neurons located in the hereinabove coordinates projects to the anterior commissure. In some embodiments, inhibiting insular neurons located in the hereinabove coordinates projects to the amygdala. In some embodiments, inhibiting insular neurons located in the hereinabove coordinates projects to the entorhinal and perirhinal area. In some embodiments, inhibiting insular neurons located in the hereinabove coordinates projects to neurons located at the following coordinates ML: (0)-(+3) cm; AP: (−0.27)-(+0.8) cm; DV: (0.5)-(−1.5) cm. In some embodiments, inhibiting insular neurons located in the hereinabove coordinates projects to neurons located at the following coordinates ML: (1)-(+3) cm; AP: (−0.1)-(+1.6) cm; DV: (0)-(−2.5) cm. In some embodiments, inhibiting insular neurons located in the hereinabove coordinates projects to neurons located at the following coordinates ML: (1)-(+3) cm; AP: (−1.2)-(+2.6) cm; DV: (−1)-(−3.5) cm. In some embodiments, inhibiting insular neurons located in the hereinabove coordinates projects to neurons in the anterior commissure located at the following coordinates ML: (0)-(+3) cm; AP: (−0.27)-(+0.8) cm; DV: (0.5)-(−1.5) cm. In some embodiments, inhibiting insular neurons located in the hereinabove coordinates projects to neurons in the amygdala located at the following coordinates ML: (1)-(+3) cm; AP: (−0.1)-(+1.6) cm; DV: (0)-(−2.5) cm. In some embodiments, inhibiting insular neurons located in the hereinabove coordinates projects to neurons in the entorhinal and perirhinal area located at the following coordinates ML: (1)-(+3) cm; AP: (−1.2)-(+2.6) cm; DV: (−1)-(−3.5) cm. In some embodiments, inhibiting insular neurons located in the hereinabove coordinates projects to neurons in the anterior commissure located at the following coordinates ML: (0)-(3) cm; AP: (−0.27)-(+0.8) cm; DV: (0.5)-(−1.5) cm and to neurons in the amygdala located at the following coordinates ML: (1)-(+3) cm; AP: (−0.1)-(+1.6) cm; DV: (0)-(−2.5) cm. In some embodiments, inhibiting insular neurons located in the hereinabove coordinates projects to neurons in the anterior commissure located at the following coordinates ML: (0)-(+3) cm; AP: (−0.27)-(+0.8) cm; DV: (0.5)-(−1.5) cm and to neurons in the entorhinal and perirhinal area located at the following coordinates ML: (1)-(+3) cm; AP: (−1.2)-(+2.6) cm; DV: (−1)-(−3.5) cm. In some embodiments, inhibiting insular neurons located in the hereinabove coordinates projects to neurons in the amygdala located at the following coordinates ML: (1)-(+3) cm; AP: (−0.1)-(+1.6) cm; DV: (0)-(−2.5) cm and to neurons in the entorhinal and perirhinal area located at the following coordinates ML: (1)-(+3) cm; AP: (−1.2)-(+2.6) cm; DV: (−1)-(−3.5) cm. In some embodiments, inhibiting insular neurons located in the hereinabove coordinates projects to neurons in the anterior commissure located at the following coordinates ML: (0)-(+3) cm; AP: (−0.27)-(+0.8) cm; DV: (0.5)-(−1.5) cm, to neurons in the amygdala located at the following coordinates ML: (1)-(+3) cm; AP: (−0.1)-(+1.6) cm; DV: (0)-(−2.5) cm and to neurons in the entorhinal and perirhinal area located at the following coordinates ML: (1)-(+3) cm; AP: (−1.2)-(+2.6) cm; DV: (−1)-(−3.5) cm.

By another aspect, there is provided a method for treating a bowel disease in a subject, the method comprising inhibiting or activating neurons in the anterior commissure, neurons in the amygdala, neurons in the entorhinal and perirhinal area, or a combination thereof. In some embodiments, the method comprises treating a bowel disease in a subject, comprising inhibiting or activating neurons in the anterior commissure located at the following coordinates ML: (0)-(+3) cm; AP: (−0.27)-(+0.8) cm; DV: (0.5)-(−1.5) cm, neurons in the amygdala located at the following coordinates ML: (1)-(+3) cm; AP: (−0.1)-(+1.6) cm; DV: (0)-(−2.5) cm, neurons in the entorhinal and perirhinal area located at the following coordinates ML: (1)-(+3) cm; AP: (−1.2)-(+2.6) cm; DV: (−1)-(−3.5) cm, or a combination thereof.

As used herein, the term "neuron activity" encompasses neuron action potential rates, action potential frequency, synapse connectivity level, rates of projection to non-insular neurons, electric excitatory activity (i.e., excitation) of insular and/or non-insular neurons, electric inhibitory activity (i.e., suppression) of insular and/or non-insular neurons, electric conductivity, rates of neurotransmitters release and/or production, types of neurotransmitters released and/or produced, tonic or regular spiking activity, phasic or bursting activity, fast spiking activity, or any combination thereof. Methods for determining neuron activity, as specified hereinabove are common and would be apparent to one of ordinary skill in the art.

As used herein, the term "project" or "projection" refer to a neuron cell activating or inhibiting a subsequent cell. In some embodiments, the insular neuron project to another insular neuron. In some embodiments, the insular neuron projects to a non-insular neuron. For example, an insular neuron projects to a neuron of the anterior commissure encompasses activation or inhibition of the anterior commissure neuron under the control of or attributed the insular neuron.

In another embodiment, the present invention is directed to a method for inhibiting an immune response comprising a step of altering activity of insular neurons. In another embodiment, the method comprises altering activity of insular neurons so as to inhibit an immune response in a specific and homeostatic manner.

In another embodiment, modulating (e.g., inhibiting) the activity of insular neurons increases the number of γδ T-cells and dendritic cells. In another embodiment, inhibiting the activity of insular neurons increases γδ T-cells and dendritic cells in a target-specific site, including but not limited to, the gut intraepithelial layer and/or the gut lamina propria.

In another embodiment, modulating (e.g., inhibiting) the activity of insular neurons reduces the level of CD4 and CD45+ T-cells. In another embodiment, inhibiting the activity of insular neurons reduces CD4 and CD45+ T-cells in a target-specific site, including but not limited to, the gut intraepithelial layer and/or the gut lamina propria.

In another embodiment, modulating (e.g., inhibiting) the activity of insular neurons reduces the level of B-cells. In another embodiment, inhibiting the activity of insular neurons reduces B-cells levels in a target-specific reduction, including but not limited to, the gut intraepithelial layer and/or the gut lamina propria In another embodiment, modulating (e.g., inhibiting) the activity of insular neurons alters (e.g., reduces) distribution of specific immune cells in the gut intraepithelial layer. In another embodiment, modulating (e.g., inhibiting) the activity of insular neurons alters (e.g., reduces) activity of specific immune cells in the gut intraepithelial layer. In another embodiment, modulating (e.g., inhibiting) the activity of insular neurons alters (e.g., reduces) distribution of specific immune cells in the gut lamina propria. In another embodiment, modulating (e.g., inhibiting) the activity of insular neurons alters (e.g., reduces) activity of specific immune cells in the gut lamina propria.

In another embodiment, the term "reducing" is inhibiting. In another embodiment, the term "reducing" is differentially inhibiting. In another embodiment, reducing an immune response includes the activation and/or induction of certain immune cells or sub-sets thereof, while at the same time inhibiting other immune cells or particular sub-sets thereof.

In another embodiment, reducing an immune response is modulating the activity, the abundance or both of a natural killer cell, a CD8 T-cell, a CD4 T-cell, a B-cell, a Dendritic cell, a basophil, a mast cell, an eosinophil, a plasma cell, an antigen presenting cell (APC), a platelet or any combination thereof. In another embodiment, modulating the activity is priming an immune cell towards a specific target. In another embodiment, modulating the activity is elevation of B-cell count in the blood, spleen and/or bone marrow.

In another embodiment, the term "modulating" is altering. In another embodiment, the term "modulating" is activating. In another embodiment, the term "modulating" is inhibiting. In another embodiment, the term "modulating" is increasing. In another embodiment, the term "modulating" is inducing. In another embodiment, the term "modulating" is elevating. In another embodiment, the term "modulating" is reducing. In another embodiment, the term "modulating" is differentially activating. In another embodiment, the term "modulating" is decreasing. In another embodiment, the term "modulating" is inhibiting. In another embodiment, the term "modulating" is differentially inhibiting.

In another embodiment, the invention provides a method of inhibiting the activity of neurons in the insula of the subject. In another embodiment, inhibiting the activity of neurons in the insula of the subject results in reduction of NK cells. In another embodiment, inhibiting the activity of neurons in the insula of the subject results in reduction of NK cells number. In another embodiment, inhibiting the activity of neurons in the insula of the subject results in reduction of B cells. In another embodiment, inhibiting the activity of neurons in the insula of the subject results in reduction of B cells number. In another embodiment, inhibiting the activity of neurons in the insula of the subject results in modulation (e.g. increase in number and/or activity) of dendritic cells. In another embodiment, inhibiting the activity of neurons in the insula of the subject results in modulation of dendritic cells number.

In another embodiment, inhibiting the activity of neurons in the insula of the subject results in reduction of CD45+ cells in the intestinal intraepithelial layer. In another embodiment, inhibiting the activity of neurons in the insula of the subject results in reduction of CD8+ cells in the intestinal intraepithelial layer. In some embodiments, the reduction of CD8+ cells in the intestinal intraepithelial layer is relatively to the total number of T cells. In another embodiment, inhibiting the activity of neurons in the insula of the subject results in induction of CD69+ expression/presentation on CD8+ cells in the intestinal intraepithelial layer. In another embodiment, inhibiting the activity of neurons in the insula of the subject results in increase of γδT cells in the intestinal intraepithelial layer. In another embodiment, the increase of γδT cells in the intestinal intraepithelial layer is relatively to the total number of immune cells. In another embodiment, the increase of γδT cells in the intestinal intraepithelial layer is relatively to the total number of CD45+ cells. In another embodiment, inhibiting the activity of neurons in the insula of the subject results in reduction of CD8+ cells in the lamina propria. In another embodiment, inhibiting the activity of neurons in the insula of the subject results in reduction of CD45+ cells in the lamina propria. In another embodiment, inhibiting the activity of neurons in the insula of the subject results in increase of γδT cells in the lamina propria. In another embodiment, inhibiting the activity of neurons in the insula of the subject results in increase of CD11b+CD103+ cells in the lamina propria. In another embodiment, the increase of CD11b+CD103+ cells is relatively to CD45+ cells.

As used herein, the CD45 cell surface molecule is presented on a T lymphocyte (CD45+ T cell). In some embodiments, the CD8 cell surface molecule is presented on a T lymphocyte (CD8+ T cell). In some embodiments, the CD45 cell surface molecule is presented on a cytotoxic T lymphocyte. In some embodiments, the CD8 cell surface molecule is presented on a cytotoxic T lymphocyte. In some embodiments, the CD45 and CD8 cell surface molecules are presented on a T lymphocyte (CD45+CD8+ T cell). In some embodiments, the CD45 and CD8 cell surface molecules are presented on a cytotoxic T lymphocyte. In some embodiments, a CD45+CD8+ T cell is a cytotoxic T lymphocyte. In some embodiments, the CD45 cell surface molecule is presented on a B lymphocyte (CD45+ B cell). In some embodiments, the CD11b cell surface molecule is presented on a monocyte (CD11b+). In some embodiments, the CD11b cell surface molecule is presented on a monocyte or a dendritic cell (CD11b+). In some embodiments, the CD103 cell surface molecule is presented on a monocyte or a dendritic cell (CD103+). In some embodiments, the CD11b and CD103 cell surface molecules are presented on a monocyte or a dendritic cell (CD11b+CD103+). In some embodiments, CD69 is presented on a T lymphocyte (CD69+ T cell). In some embodiments, CD69 is presented on a NK. In some embodiments, CD69+ cell is an activated T lymphocyte. In some embodiments, CD69+ is an activated NK. In some embodiments, CD69+ T cell is a cytotoxic T lymphocyte. In some embodiments, CD69+ is an activated T lymphocyte. In some embodiments, CD69+ is a T lymphocyte presenting CD8+ (CD8+CD69+ T cell). In some embodiments, CD69+ T lymphocyte is a differentiating or differentiation-promoting T lymphocyte. In some embodiments, CD69+ T lymphocyte is a migrating T lymphocyte. In some embodiments, CD69+ T lymphocyte is an infiltrating T lymphocyte.

In another embodiment, inhibiting the activity of neurons in the insula of the subject results in modulation of immune cells in the intestinal intraepithelial layer. In another embodiment, inhibiting the activity of neurons in the insula of the subject results in modulation of immune cells in the intestinal lamina propria. In another embodiment, inhibiting the activity of neurons in the insula of the subject results in modulation of immune cells in the spleen.

In another embodiment, an immune response is any response taken by the body to defend itself from pathogens or abnormalities. In another embodiment, an immune response is any response activating or inhibiting the immune system or mediators of the immune system. In another embodiment, immune response is an inflammatory response. In some embodiments, an inflammatory response comprises a pro-inflammatory state. In another embodiment, an immune response is an inflammatory-related response. In another embodiment, an immune response is an inflammatory response. In another embodiment, an immune response is an inflammatory disease. In another embodiment, an immune response is an autoimmune response. In another embodiment, an immune response is an autoimmune disease. In another embodiment, an autoimmune disease is an auto inflammatory disease. In another embodiment, an immune response is activation of an immune cell. In another embodiment, activation of an immune cell results in the proliferation of a sub-set of immune cells. In another embodiment, activation of an immune cell results in increased secretion of immunologic mediators by the activated cell. In another embodiment, activation of an immune cell results in the engulfment and or destruction of a pathogen or a foreign cell or molecule. In another embodiment, activation of an immune cell results in the engulfment and or destruction of a host cell such as but not limited to a cell infected by a virus. In some embodiments, activation of an immune cell reduces a systemic immune response. In some embodiments, activation of an immune cell reduces cytotoxic activity. In some embodiments, activation of an immune cell reduces the level of pro-inflammatory signals, such as pro-inflammatory cytokines. In some embodiments, activation of an immune cell increases the level of anti-inflammatory signals, such as anti-inflammatory cytokines.

In another embodiment, an immune response is any response activating or inhibiting: B cells, dendritic cells, macrophages, natural killer (NK) cells, T cells, Thymocytes, or any combination thereof. In another embodiment, a response activating or inhibiting a cell as described herein, results in: proliferation of the cell or another immune cell, inhibiting the proliferation of the cell or another immune cell, secretion of immune mediators such as cytokines and antibodies, migration of an immune cell, maturation of granulocytes, activation of an immune cascade, elimination of foreign molecules or cells, or any combination thereof.

In another embodiment, an immune response is associated with a disease and a method described herein is used to optimize the immune response according to the exact condition.

In one embodiment, the disease is an autoimmune disease. In another embodiment, the disease is Addison's disease. In another embodiment, the disease is Celiac. In another embodiment, the disease is Dermatomyositis. In another embodiment, the disease is Graves' disease. In another embodiment, the disease is Hashimoto's thyroiditis. In another embodiment, the disease is Multiple sclerosis. In another embodiment, the disease is Myasthenia gravis. In another embodiment, the disease is Pernicious anemia. In another embodiment, the disease is Reactive arthritis. In another embodiment, the disease is Rheumatoid arthritis. In another embodiment, the disease is Sjogren syndrome. In another embodiment, the disease is Systemic lupus erythematosus. In another embodiment, the disease is Type I diabetes. In another embodiment, the disease is an inflammatory disease. In another embodiment, the disease is an inflammatory bowel disease (IBD). In another embodiment, the disease is Crohn's disease. In another embodiment, the disease is ulcerative colitis (UC). In another embodiment, the disease is functional gastrointestinal disease (FGID). In another embodiment, the disease is irritable bowel syndrome (IBS). In some embodiments, IBS is IBS with predominant constipation (IBS-C). In some embodiments, IBS is IBS with predominant diarrhea (IBS-D). In some embodiments, IBS is IBS with mixed bowel habits (IBS-M). In some embodiments, IBS is IBS unclassified (IBS-U). IBS as used herein, can be determined according to the most updated version of the Rome criteria, which are incorporated herein by reference, or any equivalent standard or methodology thereof, or any equivalent standard thereto.

The terms, "Rome criteria", "Rome process" and "Rome classification" are interchangeable.

In another embodiment, the disease is an immune system disorder. In another embodiment, an immune system disorder is associated with abnormally low activity or overactivity of the immune system. In cases of immune system overactivity, the body attacks and damages its own tissues and/or cells (autoimmune diseases). In another embodiment, the disease is an immune deficiency disease such as the acquired immunodeficiency syndrome (AIDS). In another embodiment, the disease is an allergy. In another embodiment, the disease is asthma. In another embodiment, the disease is an inflammatory disease.

In another embodiment, an immune response is associated with a vaccine and a method described herein is used to optimize vaccination and the immune response associated with same. In another embodiment, an immune response is associated with cancer therapy wherein an immune response is triggered against tumor/cancer cells or cancer/tumor antigens.

The present invention provides a method for reducing body weight loss in a subject in need thereof, comprising the step of inhibiting the activity of neurons in the insular cortex of the subject, thereby reducing body weight loss in the subject.

The present invention provides a method for reducing symptoms of a subject afflicted with IBD such as reduced body weight, comprising the step of inhibiting the activity of neurons in the insular cortex of the subject, thereby reducing symptoms of a subject afflicted with IBD.

As defined herein, "weight loss" refers to unintentional or symptomatic weight loss in a subject afflicted by a disease e.g., IBD, IBS, etc. In one embodiment, weight loss refers to unintentional reduction of at least 3% of whole body weight in a subject. In another embodiment, weight loss refers to unintentional reduction of at least 4% of whole body weight in a subject. In another embodiment, weight loss refers to unintentional reduction of at least 5% of whole body weight in a subject. In another embodiment, weight loss refers to unintentional reduction of at least 10% of whole body weight in a subject. In another embodiment, weight loss refers to unintentional reduction of at least 20% of whole body weight in a subject. In another embodiment, weight loss refers to unintentional reduction of at least 30% of whole body weight in a subject. In another embodiment, weight loss refers to unintentional reduction of at least 40% of whole body weight in a subject. In another embodiment, weight loss refers to unintentional reduction of at least 50% of whole body weight in a subject. In some embodiments, weight loss is unintentional reduction of 1-7%, 4-12%, 5-15%, 8-20%, 15-23%, 20-32%, 27-40%, 25-45%, 40-55%. Each possibility represents a separate embodiment of the invention.

As used herein, "colon shortening" refers to reduction in colon length, width, or a combination thereof. In some embodiments, the colon shortening is a result of inflammation. In another embodiment, the reduction in colon width is a result of inflammation. In another embodiment, a shorten colon is shorter than a normal colon's length. In another embodiment, a shorten colon is narrower than a normal colon's width. In another embodiment, a shorter colon is shorter by at least 1%. In another embodiment, a shorter colon is shorter by more than 2.5%. In another embodiment, a shorter colon is shorter by more than 5%. In another embodiment, a shorter colon is shorter by more than 7.5%. In another embodiment, a shorter colon is shorter by more than 10%. In another embodiment, a shorter colon is shorter by more than 20%. In some embodiments, colon shortening is by 1-5%, 1.5-4%, 2-8%, 3-12%, 5-15%, 7-18%, or 5-20%. Each possibility represents a separate embodiment of the invention.

In another embodiment, a subject is a mammal. In another embodiment, a subject is a human subject. In another embodiment, a subject is a farm animal. In another embodiment, a subject is a pet. In another embodiment, a subject is a lab animal. In another embodiment, a subject is a rodent.

In some embodiments, the subject has a pro-inflammatory state.

The term "inflammation" as used herein refers to the general medical sense of the word and may be an acute or chronic; simple or suppurative; localized or disseminated; cellular and tissue response, initiated or sustained by any number of chemical, physical or biological agents or combination of agents.

As used herein, the term "inflammatory state" indicates the relative biological condition of a subject resulting from inflammation, or characterizing the degree of inflammation.

In some embodiments, the method comprises a step of detecting a pro-inflammatory state of the subject. As used herein, determining comprises determining the expression level of one or more pro-inflammatory markers selected from Table 1 (hereinbelow). In some embodiments, an increase of at least 5% in the expression level of one or more pro-inflammatory markers compared to a non-inflammatory control, indicates the subject has a pro-inflammatory state. In some embodiments, a subject determined as having a pro-inflammatory state is suitable for a treatment according to the method of the disclosed invention.

In some embodiments, an increase of at least 5% comprises at least 6% more, at least 10% more, at least 20% more, at least 50% more, at least 100% more, at least 250% more, at least 500% more, at least 750% more, at least 1,000% more, or any value or range therebetween. In some embodiments, an increase of at least 5% comprises 5-10% more, 5-20% more, 15-40% more, 35-80% more, 75-150% more, 100-250% more, 200-450% more, 400-800% more, or 750-1,000% more. Each possibility represents a separate embodiment of the invention.

As used herein a subject having pro-inflammatory state comprises increased expression levels of one or more markers selected from Table 1 (hereinbelow). As used herein, the term "increased expression" is compared to a control. In some embodiments, the control is a non-pro-inflammatory control. In some embodiments, the control is a sample derived or obtained from the subject before the subject has been afflicted by a pro-inflammatory state, an inflammatory disease, or both. In some embodiments, the control is a sample derived or obtained from a healthy subject.

As used herein, a sample comprises a bodily fluid. In some embodiments, a sample comprises a tissue, a fragment thereof, a portion thereof, or any combination thereof in some embodiments, a sample is a tissue extract or a fraction thereof.

As used herein, the term "bodily fluid" encompasses any fluid obtained from a living organism. In one embodiment, bodily fluid comprises serum. In one embodiment, bodily fluid comprises plasma. Other non-limiting examples for bodily fluids include, but are not limited to, vitreous fluid, lymph fluid, synovial fluid, follicular fluid, seminal fluid, amniotic fluid, milk, whole blood, urine, cerebrospinal fluid, saliva, sputum, tears, perspiration, mucus, and tissue culture media, including tissue extracts such as homogenized tissue, and cellular extracts. Methods for obtaining a biological sample are well within the capabilities of those skilled in the art.

In some embodiments, the sample comprises any one of a polynucleotide molecule, and a peptide molecule. As used herein, a polynucleotide molecule comprises DNA, RNA, or hybrids thereof. A peptide as used herein, comprises any amino acid-comprising polymer comprising two or more amino acids, e.g., peptide, polypeptide, and a protein.

In some embodiments, one or more pro-inflammatory markers comprises at least 2, at least 3, at least 4, at least 5, at least 7, at least 10, at least 12, at least 15, at least 20, at least 22, at least 26, at least 30, at least 33, at least 36, at least 41, at least 45, at least 47 pro-inflammatory markers, or any value or range therebetween. In some embodiments, one or more pro-inflammatory markers comprises 1-5, 2-7, 6-11, 10-14, 12-17, 16-22, 19-30, 18-35, 28-41, 33-40, 36-43, or 40-48 pro-inflammatory markers. Each possibility represents a separate embodiment of the invention.

TABLE 1

Pro-inflammatory markers
Pro-inflammatory marker

| Code | Full name |
|---|---|
| IL1A | Interleukin 1 alpha |
| IL1B | Interleukin 1 beta |
| TNFA | Tumor necrosis factor alpha |
| IL6 | Interleukin 6 |
| IL8 | Interleukin 8 |
| IFNG | Interferon gamma |
| IL2 | Interleukin 2 |
| IL12B | Interleukin 12 beta |
| IL15 | Interleukin 15 |
| IL18 | Interleukin 18 |
| IL4 | Interleukin 4 |
| IL5 | Interleukin 5 |
| IL10 | Interleukin 10 |
| IL13 | Interleukin 13 |
| IL1RN | Interleukin 1 receptor antagonist |
| IL18BP | Interleukin 18 binding protein |
| TGFB1 | Transforming growth factor beta 1 |
| IFNA2 | Interferon alpha-2 |
| GRO1 | Chemokine ligand 1 |
| GRO2 | Chemokine ligand 2 |
| TNFSF5 | CD40 ligand |
| TNFSF6 | Fas ligand |
| CSF3 | Colony-stimulating factor 3 |
| B7 | CD80 |
| CSF2 | Colony-stimulating factor 2 |
| TNFSF13B | Tumor necrosis factor ligand member 13b |
| TACI | Tachykinin Precursor 1 |
| VEGF | Vascular endothelial growth factor |
| ICAM1 | Intercellular Adhesion Molecule 1 |
| PTGS2 | Prostaglandin-Endoperoxide Synthase 2 |
| NOS2A | Nitric oxide synthase 2a |
| PLA2G7 | Phospholipase A2 Group VII |
| HMOX1 | Heme Oxygenase 1 |
| CD3Z | T-cell receptor T3 zeta chain |
| PTPRC | Protein Tyrosine Phosphatase |
| CD14 | Cluster of differentiation 14 |
| CD4 | Cluster of differentiation 4 |
| CD8A | Cluster of differentiation 8A |
| CD19 | Cluster of differentiation 19 |
| HSPA1A | Heat Shock Protein Family A (Hsp70) Member 1A |
| MMP3 | Matrix metalloproteinase-3 |
| MMP9 | Matrix metallopeptidase 9 |
| PLAU | Plasminogen Activator, Urokinase |
| SERPINE1 | (Serpin Family E Member 1 |
| TIMP1 | Tissue inhibitor of metalloproteinases 1 |
| C1QA | Complement C1q subcomponent subunit A |
| HLA-DRB1 | HLA class II histocompatibility antigen, DRB1 beta chain |

The term "expression" as used herein, refers to the gene product and/or the protein product, and encompasses gene expression level, transcript level, transcription rate or level, protein synthesis rate, protein amount, protein secretion, or any combination thereof.

Methods for obtaining a sample comprising polynucleotides and/or peptides and subsequently determining the expression levels of a specific marker within the sample are common and would be apparent to one of ordinary skill in the art.

Non-limiting examples include, but are not limited to, RNA extraction followed by reverse transcription and PCR (such as RT-PCR, real time PCR), western-blot, SDS-PAGE, densitometry, flow cytometry, microarray, hybridization assays, enzyme linked immunosorbent assay (ELISA, such as direct or indirect ELISA), and others, all of which would be apparent to a skilled artisan.

In another embodiment, inhibiting neuronal activity is by means of magnetic stimulation using induced currents. In another embodiment, TMS is a time-varying pulse of current in an external coil causing inducing currents in the brain. In another embodiment, magnetic stimulation is used for electrical stimulation of nerves in the insular cortex.

In another embodiment, TMS can be substituted with cranial electrotherapy stimulation. In another embodiment, TMS can be substituted with transcranial direct current stimulation. In another embodiment, TMS can be substituted with electroconvulsive therapy. In another embodiment, TMS can be substituted with biofeedback. In another embodiment, TMS can be substituted with focused ultrasound modulation. All of the hereinabove substitutions are applicable as long as they maintain/achieve the bowel disease therapeutic effect and/or inhibition of insular neurons activity.

In another embodiment, a TMS of the invention includes stimulating coil geometry of a circle or a 'figure-of-eight'. In another embodiment, a TMS of the invention run at tens of stimuli per second. In another embodiment, TMS stimulation is delivered to a single cortical target using the same coil. In another embodiment, multiple stimuli of TMS are delivered in trains. In another embodiment, 'high-frequency' repetitive TMS (rTMS) is utilized according to the invention. In another embodiment, a theta burst (TBS) protocol providing short bursts of 50 Hz rTMS is used at a rate in the theta range (5 Hz) as a continuous (cTBS), or intermittent (iTBS) train. In another embodiment, quadripulse stimulation (QPS) is applied (patterned rTMS procedure able to induce long-term changes of cortical excitability). All of the herein above TMS options are applicable as long as they maintain/achieve the bowel disease therapeutic effect and/or inhibition of insular neurons activity.

In another embodiment, a TMS includes a coil for magnetic stimulation positionable on a head part. In another embodiment, a TMS includes a coil for magnetic stimulation positionable on a head part for stimulating a deep brain region. In another embodiment, the coils are oriented such that they will produce a considerable field in a direction tangential to the surface, which should also be the preferable direction to modulate the insular neurons. In another embodiment, the wires of the coils are directed in one or more directions, which results in a preferred modulation of insular neuronal structures. In another embodiment, deep TMS according to the invention provide deep region modulation without causing a large electrical field at surface areas of the brain. All of the hereinabove coil physical characteristics, structures, etc. are applicable as long as they maintain/achieve the bowel disease therapeutic effect and/or inhibition of insular neurons activity.

In another embodiment, inhibition is by means of biofeedback. As defined herein, "biofeedback" refers to a technique of making available to a subject a record of one or more of the subject's physiological activities to which the subject ordinarily does not have direct conscious access. In another embodiment, biofeedback is an EEG (electroencephalogram) biofeedback. As used herein, "EEG biofeedback" refers to a subject's EEG activity as the physiological system that is used for biofeedback. In another embodiment, an EEG waveform vary in frequency of 0.01 to 100 Hz. In another embodiment, an EEG is recorded from an electrode sensor placed on or in the brain. In another embodiment, EEG is recorded from an electrode sensor placed on the scalp surface. In another embodiment, an EEG scalp sensor is known to measure ongoing, spontaneous bioelectric signals generated by underlying cerebral cortex. In another embodiment, in EEG biofeedback the brain wave profile is presented to the subject and the subject is rewarded for changing the profile. In another embodiment, a reward includes, but not limited to, a pleasant-sounding tone, a continuous tone, a dichotomous tone, a visual display, or others. Any biofeedback modality is applicable as long as it maintains/achieves the bowel disease therapeutic effect and/or inhibition of insular neurons activity.

One of ordinary skill in the art would appreciate applying biofeedback as part of medication.

In another embodiment, modulating (e.g., inhibiting) is by means of focused ultrasound stimulation (FUS) using induced sound waves. In some embodiments, stimulation comprises a low intensity focused ultrasounds (LIFU). In some embodiments, stimulation comprises a high intensity focused ultrasounds (HIFU). In some embodiments, the ultrasound energy source is used to deliver the treatment energy to the nerve from multiple directions outside the subject. In some embodiments, the treatment energy is delivered to modulate the nerve without damaging the nerve. Any intensity focused ultrasound is applicable as long as it maintains/achieves the bowel disease therapeutic effect and/or the inhibition of insular neurons activity.

In one embodiment, a focused ultrasound stimulation (FUS) is delivered using a standardized device, operable as known to one skilled in the art. In one embodiment, a FUS device is comprised of a detector to determine the location of the nerve from a position external to a subject. In another embodiment, a FUS device is comprised of an ultrasound component to deliver therapeutic energy through the skin from at least two directions to the nerve. In another embodiment, a FUS device is comprised of a modeling algorithm comprising an input and an output, the input to the modeling algorithm comprising a three-dimensional coordinate space containing a therapeutic energy source and the position of the nerve center in the three-dimensional coordinate space. In another embodiment, the output from the modeling algorithm is comprised of the direction and energy level of the ultrasound component.

In some embodiments, a method comprising a FUS for inhibiting the function or activity of a nerve cell is provided. As known by one skilled in the art, the location of a nerve center of a subject is determined by an external imaging modality. In one embodiment, the nerve center is placed in a first three-dimensional coordinate reference based on the imaging. In one embodiment, a therapeutic energy generation source is placed or associated in the first three-dimensional coordinate reference frame. In one embodiment, a delivery of energy to the insular region where a specific nerve center is located is modeled. In another embodiment, therapeutic energy from the therapeutic energy source is delivered from at least two different angles, through the skin of a subject. In another embodiment, therapeutic delivery of a therapeutic energy at least partially inhibits the function or activity of the nerve center within the insular cortex.

In some embodiments, the focus for stimulation is described as two or more centimeters deep and 0.5 to 1,000 mm in diameter. In another embodiment, the focus for stimulation is in the range of 2-12 cm deep and 0.5-2 mm in diameter. In one embodiment the focus diameter is in the range of 0.5-500 mm. In another embodiment, the focus diameter is in the range of 500-1,500 mm. In one embodiment, low frequencies are defined as below 300 Hz. In another embodiment, low frequencies are inhibitory and inhibit neural circuits. In one embodiment, high frequencies are defined as being in the range of 500 Hz to 5 MHz. In another embodiment, high frequencies are excitatory and activate neural circuits. Any diameter is applicable as long as the bowel disease therapeutic effect and/or inhibition of insular neuron activity is maintained/achieved.

In some embodiments, LIFU ranges from 30-500 mW/cm$^2$. In some embodiments, LIFU ranges from 35-300 mW/cm$^2$. In some embodiments, LIFU ranges from 100-250 mW/cm$^2$. In some embodiments, LIFU ranges from 75-450 mW/cm$^2$. In some embodiments, LIFU ranges from 150-475 mW/cm$^2$. In some embodiments, HIFU requires power levels exceeding 100 W/cm$^2$. In some embodiments, HIFU requires power levels exceeding 300 W/cm$^2$. In some embodiments, HIFU requires power levels exceeding 100 W/cm$^2$. In some embodiments, HIFU requires power levels exceeding 500 W/cm$^2$. In some embodiments, HIFU requires power levels exceeding 750 W/cm$^2$. In some embodiments, HIFU requires power levels exceeding 1 kW/cm$^2$. In some embodiments, HIFU requires power levels exceeding 10 kW/cm$^2$. In some embodiments, HIFU requires power levels exceeding 100 kW/cm$^2$. In some embodiments, HIFU requires power levels exceeding 500 kW/cm$^2$. In some embodiments, HIFU ranges from 0.1-500 kW/cm$^2$. In one embodiment, ultrasound is the energy used to inhibit nerve conduction in a nerve cell. In one embodiment, HIFU from outside the body through the skin is the energy used to inhibit neural stimulation. In one embodiment, LIFU is sufficient to stun or partially inhibit specific nerves particularly when pulsed and depending on the desired clinical result. In another embodiment, a train of pulses is utilized to augment the effect on nervous tissue. In another embodiment, a train of 100 short pulses, each less than a second and applying energy densities of 1 W/cm$^2$ to 500 W/cm$^2$ is applied. In some of the embodiments, cooling may be applied to the skin if the temperature rise is deemed too large to be acceptable. In some embodiments, the energy is delivered in a pulsed fashion. In another embodiment, the pulses can be as frequent as millisecond, seconds and tens of seconds. In another embodiment, the pulses can be delivered in intervals of hours, days or years. Any HIFU or LIFU power level, pulse frequency, and number of pulses per a defined time period are applicable as long as the bowel disease therapeutic effect and/or the inhibition of insular neuron activity is maintained/achieved.

By another aspect, there is provided a system comprising a transcranial stimulation transducing coil for transcranial stimulation configured to provide a series of pulses to neurons of the insular cortex of a subject. In some embodiments, the system is configured to provide a series of pulses to neurons of the insular cortex located in coordinates: ML: (2.5)-(+4.5) cm; AP: (3.0)-(−2.2) cm; and DV: (−1)-(+2) cm.

In some embodiments, the system is for use in inhibiting the activity of neurons of the insular cortex using transcranial stimulation (TS) (e.g., transcranial magnetic stimulation, TMS). In some embodiments, the system is for use in treating a bowel disease using transcranial stimulation (e.g., TMS). TMS is a proven and safe technique for the non-invasive stimulation of neurons and has been shown to be beneficial in the treatment of a variety of disorders such as neurological disorders (e.g., depression).

In some embodiments, the system is a system for deep stimulation. In some embodiments, the system comprises a standard coil or any other coil suitable for TS is provided. In some embodiments, the TS system is positioned on the skull, on or adjacent to the area of the brain to be treated, and stimulating pulses (e.g., electric, magnetic, sound, etc.) are provided via the disclosed TS system. In some embodiments, a series of pulses is provided using a prescribed TS coil configuration in conjunction with a prescribed range of frequencies and stimulation amplitudes.

Different ranges of frequency, amplitudes and numbers of pulses and combinations thereof may be used, correlating with the severity of symptoms and/or the disease state, which would be apparent to one of ordinary skill in the art.

In some embodiments, the system is an electric stimulation system. In some embodiments, the system is a magnetic stimulation system. In some embodiments, the system is a sound stimulation system. In some embodiments, the system is a light stimulation system. In some embodiments, the system is a multiple stimulation system, comprising an electric stimulating transducer, a magnetic stimulating transducer, a sound stimulating transducer, a light stimulating transducer, or any combination thereof.

As used herein, sound stimulation comprises ultrasound stimulation and/or an ultrasound source.

In some embodiments, a system providing light stimulation comprises a laser as a light source.

In some embodiments, the system comprises a control unit.

In some embodiments, the control unit may modulate a series of pulses provided. In one embodiment, the control unit may regulate the amplitude of the pulse. In one embodiment, the control unit may regulate the frequency of the pulse. In one embodiment, the control unit may regulate duration of the pulse.

In one embodiment, the control unit may regulate the DC or the AC current, the amperes per meter, the wavelength of an emitted light, the Hz frequency, or a combination thereof. Each possibility represents a separate embodiment of the invention.

In some embodiments, the system further comprises a computer program product.

Optionally, the computer program product comprises a computer-readable storage medium. The computer-readable storage medium may have program code embodied therewith. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the drawings. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the drawings.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the drawings.

In some embodiments, the program code is excusable by a hardware processor.

In some embodiments, the hardware processor is a part of the control unit.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the term "condition" includes anatomic and physiological deviations from the normal that constitute an impairment of the normal state of the living animal or one of its parts, that interrupts or modifies the performance of the bodily functions.

Any concentration ranges, percentage range, or ratio range recited herein are to be understood to include concentrations, percentages or ratios of any integer within that range and fractions thereof, such as one tenth and one hundredth of an integer, unless otherwise indicated.

As used herein, the terms "subject" or "individual" or "animal" or "patient" or "mammal," refers to any subject, particularly a mammalian subject, for whom therapy is desired, for example, a human.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a", "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise", "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); "Bacteriophage Methods and Protocols", Volume 1: Isolation, Characterization, and Interactions, all of which are incorporated by reference. Other general references are provided throughout this document.

Example 1

Involvement of the Insular Cortex in the Gut Inflammatory Response

In order to discover whether the insula cortex is involved in the gut inflammatory response the inventors used a transgenic mice model, Fos$^{CreER}$, that enables genetic access to active neurons at a certain time window. These mice express the Cre-recombinase enzyme under the promoter of the immediate early gene, cFos, thus expressing it only in activated neurons. Tamoxifen (TM) administration allows the Cre-lox recombination to occur on our targeted gene, a gene specifically encoding for a fluorescence protein. Consequently, the fluorescence labeling occurs only in neurons that were active during the injection of TM. Injecting TM in the course of colon inflammation "tags" the neurons that were active at that time and allowed the inventors to visualize them using fluorescence microscopy (FIG. 1).

Example 2

Inhibition of Insular Activity Alleviates Gut Inflammatory Response

Figure 2A:
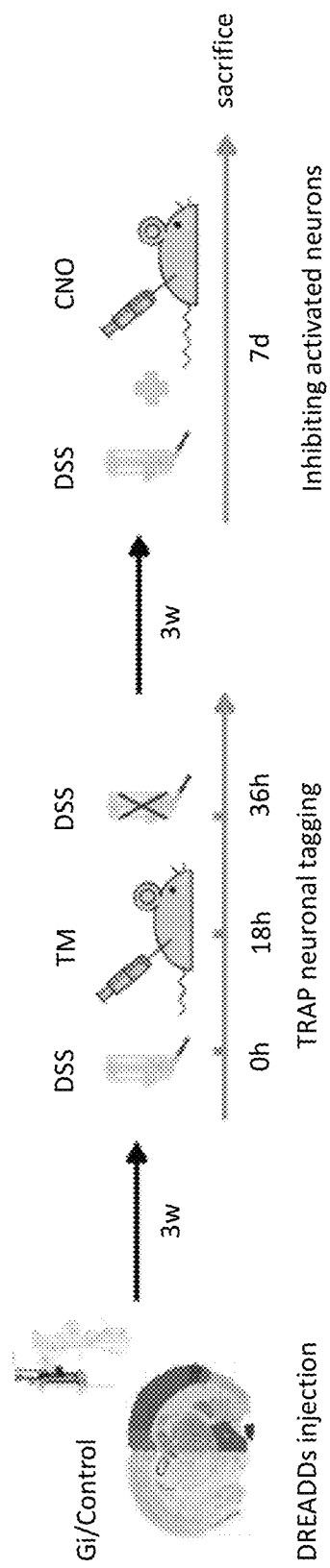
Figure 4H:

As the insula cortex was shown to be active during colon inflammation, the inventors further aimed at discovering its possible effects on immune responses. Mice were stereo tactically injected with a DREADD encoding viral vector (AAV8-hSyn-DIO-hM4D(Gi)-mCherry) and a sham vector (AAV8-hSyn-DIO-mCherry) to the control group. After recovery, mice were injected with TM during DSS administration for neuronal labeling. Three weeks later, both groups were administered with DSS for 7 days, receiving daily injections of CNO (FIG. 2A) for inhibition of the insula during the progress of inflammation. The control group suffered from severe symptoms of inflammation, including substantial weight loss, shortening of the colon and rectal bleeding. Although similar symptoms appeared in the Gi group, they were milder (FIGS. 2B and 2C). Differences between the two groups also appeared in immune cell populations levels at the inflammation site (FIGS. 2D-2K).

Example 3

Activation of the Insular Engram Induces an Inflammatory Response

To further examine the role of the insula cortex in the inflammatory response, the inventors injected mice with a stimulating DREADD (AAV8-hSyn-DIO-hM3D(Gq)-mCherry). The injected mice were randomly divided into 3 groups: expressing DREADD in neurons that were active one day before initiation of inflammation (no inflammation); 2 days after its induction (inflammation); and 7 days after its termination (after inflammation). Three weeks later, all groups were injected with CNO and sacrificed 18 h later for immune cells analysis (FIG. 3A). Flow cytometry analysis has shown a significant increase in intraepithelial layer (IEL) and lamina propria (LP) CD45$^{high}$ (i.e., CD45+) cells in the inflammation group, compared to the other two groups (FIGS. 3B-3J). This result indicated hyper-activity of the local immune response in the colon as a consequence of inflammatory-related neurons activation.

Example 4

Inhibiting Insular Hyper-Activity Using Transcranial Stimulation for Reducing Gut Inflammation Mice are injected with a stimulating DREADD (AAV8-hSyn-DIO-hM3D(Gq)-mCherry). The injected mice are randomly divided into 2 groups, both expressing DREADD in neurons that are active 2 days after induction of inflammation (using dextran sodium sulfate). Thereafter, one group is designated as control (untreated from that point onwards) and the second group is applied with TMS to the following coordinates: ML: (4.00) mm; AP: (−0.35) mm; and DV: (−3.85) mm. Three weeks later, both groups are injected with CNO and are further reared for 18 h after which animals are anesthetized, weighed, and dissected. Colons are then excised and measured (examining 'colon shortening').

Furthermore, immune cells are collected from the IPE and LP for flow cytometry analysis, specifically with the following markers: CD45, CD8, CD69, CD4, CD11, and CD103. This example shows that inhibiting hyper active neurons of the insular cortex using TS can reduce gut inflammation in mice.

Example 5

Inhibiting Insular Hyper-Activity Using Transcranial Stimulation for Reducing Gut Inflammation IBD mice, as previously described by Mizoguchi (2012), are randomly divided into 2 groups, one group is designated as control ('IBD control') and the second group is applied with TS (e.g., TMS, FUS, etc.) to the following coordinates: ML: (4.00) mm; AP: (−0.35) mm; and DV: (−3.85) mm. After 3 weeks of TS later, both groups are anesthetized, weighed, and dissected. Colons are then excised and measured (examining 'colon shortening'). Furthermore, immune cells are collected from the IPE and LP for flow cytometry analysis, specifically with the following markers: CD45, CD8, CD69, CD4, CD11, and CD103. This example shows that inhibiting hyper active neurons of the insular cortex using TS can reduce gut inflammation in a murine IBD model.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for reducing an immune response in a human subject in need thereof, the method comprising inhibiting an activity of neurons of the insular cortex of said human subject by applying any one of: transcranial magnetic stimulation (TMS), biofeedback stimulation, focused ultrasound stimulation (FUS), and electrical stimulation to neurons of the insular cortex of said human subject so as to inhibit said activity of said neurons, wherein said inhibiting the activity of neurons of the insular cortex is reducing the number of: CD4 and CD45+ T cells, B cells, or any combination thereof, in an intraepithelial layer or lamina propria of said human subject.

2. The method of claim 1, wherein said neurons of the insular cortex of said human subject correspond to neurons of a murine insular cortex located in murine brain coordinates:
  a) Medial Lateral (ML): +4 mm;
  b) Anterior Posterior (AP): 0.3 mm; and
  c) Dorsal Ventral (DV): 3.85 mm.

3. The method of claim 1, wherein said human subject is afflicted with Crohn's disease.

4. The method of claim 1, wherein said human subject is afflicted with ulcerative colitis (UC).

5. The method of claim 1, wherein said human subject is afflicted with an immunodeficient disease.

6. The method of claim 1, wherein said human subject is afflicted with an autoimmune disease.

7. The method of claim 1, wherein said human subject is afflicted with a functional gastrointestinal disorder (FGID) or a symptom thereof.

8. The method of claim 7, wherein said FGID is irritable bowel syndrome (IBS).

9. The method of claim 1, wherein said inhibiting the activity of neurons of the insular cortex comprises altering activity, abundance or both of a CD8 T-cell, a CD4 T-cell, a γδ T-cell, a B-cell, a dendritic cell, or any combination thereof.

10. The method of claim 1, wherein said inhibiting the activity of neurons of the insular cortex further comprises increasing the number of monocyte cells, wherein said increasing is in an intraepithelial layer of said human subject.

11. The method of claim 10, wherein said monocyte cells are CD11b+ monocyte, CD103+ monocyte, or CD11b+ CD103+ monocyte.

12. The method of claim 1, wherein said inhibiting the activity of neurons of the insular cortex is increasing the number of γδT cells in a lamina propria of said human subject.

13. The method of claim 1, wherein said reducing an immune response comprises treating an immune-related disease in said human subject.

14. The method of claim 13, wherein said immune-related disease is an inflammatory disease.

15. The method of claim 13, wherein said immune-related disease is an auto inflammatory disease.

16. The method of claim 13, wherein said immune-related disease is selected from the group consisting of: inflammatory bowel disease (IBD), UC, Crohn's disease, FGID, IBS, Addison's disease, Celia, Dermatomyositis, Graves' disease, Hashimoto's thyroiditis, Multiple sclerosis, Myasthenia gravis, Pernicious anemia, Reactive arthritis, Rheumatoid arthritis, Sjogren syndrome, Systemic lupus erythematosus, and Type I diabetes.

17. The method of claim 13, wherein said immune-related disease is IBD.

18. A method for reducing an immune response in a human subject in need thereof, the method comprising the steps:
  (a) selecting a human subject afflicted with an immune-related disease; and
  (b) inhibiting an activity of neurons of the insular cortex of said human subject from step (a) by applying any one of: TMS, biofeedback stimulation, FUS, and electrical stimulation to neurons of the insular cortex of said human subject so as to inhibit said activity of said neurons, wherein said inhibiting the activity of neurons of the insular cortex is reducing the number of: CD4 and CD45+ T cells, B cells, or any combination thereof, in an intraepithelial layer or lamina propria of said human subject.

* * * * *